US00PP22116P2

(12) United States Plant Patent
Dekker

(10) Patent No.: US PP22,116 P2
(45) Date of Patent: Sep. 6, 2011

(54) ***CHRYSANTHEMUM* PLANT NAMED 'DEKSTARGA'**

(50) Latin Name: *Chrysanthemum×morifolium*
Varietal Denomination: Dekstarga

(75) Inventor: Cornelis W. Dekker, Hensbroek (NL)

(73) Assignee: Dekker Breeding, B.V., Hensbroek (NL)

( * ) Notice: Subject to any disclaimer, the term of this patent is extended or adjusted under 35 U.S.C. 154(b) by 0 days.

(21) Appl. No.: 12/798,022

(22) Filed: Mar. 27, 2010

(51) Int. Cl.
*A01H 5/00* (2006.01)

(52) U.S. Cl. ..... Plt./286

(58) Field of Classification Search ..... Plt./286, Plt./297, 287
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Dekstarga', characterized by its small anemone-type inflorescences with red purple-colored ray florets and dark purple-colored disc florets that become pale yellow in color with development; strong and upright flowering stems; uniform and freely flowering habit; and excellent postproduction longevity.

2 Drawing Sheets

Botanical designation: *Chrysanthemum×morifolium.*
Cultivar denomination: 'DEKSTARGA'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Dekstarga'.

The new *Chrysanthemum* plant is a product of a planned breeding program conducted by the Inventor in Hensbroek, The Netherlands. The objective of the breeding program is to create new anemone-type *Chrysanthemum* plants with small inflorescences with attractive ray and disc floret coloration and excellent postproduction longevity.

The new *Chrysanthemum* plant originated from a cross-pollination made by the Inventor in Hensbroek, The Netherlands on Apr. 10, 2007 of a proprietary selection of *Chrysanthemum×morifolium* identified as code number 06.53068.04, not patented, as the female, or seed, parent with a proprietary selection of *Chrysanthemum×morifolium* identified as code number 41411, not patented. The new *Chrysanthemum* plant was discovered and selected by the Inventor as a single flowering plant from within the progeny of the stated cross-pollination in a controlled greenhouse environment in Hensbroek, The Netherlands in November, 2007.

Asexual reproduction of the new *Chrysanthemum* plant by terminal cuttings in a controlled greenhouse environment in Hensbroek, The Netherlands since December, 2007, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekstarga'. These characteristics in combination distinguish 'Dekstarga' as a new and distinct *Chrysanthemum* plant:

1. Small anemone-type inflorescences with red purple-colored ray florets and dark purple-colored disc florets that become pale yellow in color with development.
2. Strong and upright flowering stems.
3 Uniform and freely flowering habit.
4. Excellent postproduction longevity; plants maintain good substance for about 21 days in an interior environment.

Plants of the new *Chrysanthemum* differ from plants of the female parent selection in the following characteristics:

1. Plants of the new *Chrysanthemum* flower seven days later than plants of the female parent selection.
2. Plants of the new *Chrysanthemum* and the female parent selection differ in ray floret color as plants of the female parent selection have white and greyed red-colored ray florets.

Plants of the new *Chrysanthemum* differ from plants of the male parent selection in the following characteristics:

1. Plants of the new *Chrysanthemum* flower five days earlier than plants of the male parent selection.
2. Plants of the new *Chrysanthemum* are more freely flowering than plants of the male parent selection.
3. Plants of the new *Chrysanthemum* have smaller inflorescences than plants of the male parent selection.

Plants of the new *Chrysanthemum* can be compared to plants of *Chrysanthemum×morifolium* 'Dekcedis', not patented. In side-by-side comparisons conducted in Hensbroek, The Netherlands, plants of the new *Chrysanthemum* differed from plants of 'Dekcedis' in the following characteristics:

1. Plants of the new *Chrysanthemum* flowered seven days later than plants of 'Dekcedis'.
2. Plants of the new *Chrysanthemum* and 'Dekcedis' differed in ray floret color as plants of 'Dekcedis' had white and greyed red-colored ray florets.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dekstarga' grown as a spray-type.

The photograph on the second sheet comprises close-up views of the upper (top of photograph) and lower surfaces (bottom of photograph) of typical inflorescences and leaves of 'Dekstarga'.

DETAILED BOTANICAL DESCRIPTION

The aforementioned photographs and following observations and measurements describe plants grown during the winter in Hensbroek, The Netherlands, under commercial practice in ground beds in a glass-covered greenhouse. Plants were initially given 1.5 weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were 7.5 weeks old when the description was taken and nine weeks old when the photographs were taken. In the following description, color references are made to The Royal Horticultural Society Colour Chart, 2007 Edition, except where general terms of ordinary dictionary significance are used.

Botanical classification: *Chrysanthemum×morifolium* 'Dekstarga'.

Parentage:

*Female, or seed, parent.*—Proprietary selection of *Chrysanthemum×morifolium* identified as code number 06.53068.04, not patented.

*Male, or pollen, parent.*—Proprietary selection of *Chrysanthemum×morifolium* identified as code number 41411, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous anemone-type cut flower that is typically grown as a spray-type; moderately vigorous growth habit.

*Flowering stem description.*—Aspect: Erect. Strength: Strong. Length: About 60 cm. Stem diameter: About 5 mm. Spray diameter: About 12 cm to 15 cm. Internode length: About 1.5 cm. Texture: Finely pubescent; longitudinally ridged. Color: Close to 146B.

*Foliage description.*—Arrangement: Alternate; simple. Length: About 5.5 cm to 8.5 cm. Width: About 3.5 cm to 5 cm. Apex: Emarginate. Base: Attenuate. Margin: Palmately lobed, serrate; sinuses parallel to divergent. Texture, upper and lower surfaces: Pubescent, slightly rough; veins prominent on lower surface. Venation pattern: Pinnate, reticulate. Color: Developing leaves, upper surface: Close to 137C. Developing leaves, lower surface: Lighter than 147B. Fully developed leaves, upper surface: Close to N137C; venation, close to 148B. Fully developed leaves, lower surface: Close to 147B; venation, close to 146B. Petiole: Length: About 0.5 cm to 2 cm. Diameter: About 2 mm to 4 mm. Texture, upper and lower surfaces: Slightly rough. Color, upper surface: Close to 146B. Color, lower surface: Close to 146B to 146C.

Inflorescence description:

*Appearance.*—Small anemone-type inflorescence form with oval-shaped ray florets and enlarged tubular disc florets; inflorescences borne perpendicular to axillary laterals (peduncles); ray and disc florets develop acropetally on a capitulum.

*Fragrance.*—Slightly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering response; plants exposed to 1.5 weeks of long day/short night conditions after planting followed by photoinductive short day/long night conditions flower about 43 days later when grown as a spray-type.

*Postproduction longevity.*—In an interior environment, inflorescences and foliage will maintain good color and substance for about 21 days; inflorescences persistent.

*Quantity of inflorescences.*—Freely flowering habit; when grown as a spray type, about 50 inflorescences develop.

*Inflorescence size.*—Diameter: About 2 cm to 2.5 cm. Depth (height): About 7 mm. Disc diameter: About 1.3 cm to 1.5 cm. Receptacle height: About 4 mm. Receptacle diameter: About 5 mm. Receptacle color: Close to 145B.

*Inflorescence buds.*—Shape: Flattened spherical. Height: About 3 mm. Diameter: About 6 mm. Color: Close to 137C.

*Ray florets.*—Length: About 5 mm to 7 mm. Width: About 3 mm to 4 mm. Shape: Oval. Apex: Emarginate. Base: Attenuate. Margin: Entire. Texture, upper and lower surfaces: Smooth, glabrous; satiny. Number per inflorescence: About 25 arranged in a single whorl. Aspect: About 30° from horizontal. Color: When opening and fully opened, upper surface: Close to 70A towards the base, close to 155D; with development, color becomes closer to 72B. When opening and fully opened, lower surface: Close to 70B towards the base, close to 155D; with development, color becomes closer to 71A.

*Disc florets.*—Shape: Fused tubular, erect and enlarged. Apex: Dentate. Length: About 4 mm to 6 mm. Diameter: About 1 mm. Number per inflorescence: About 225, massed at the center of the receptacle. Color: When opening: Apex: Close to 183B. Mid-section: Close to 3C. Base: Close to 150C. Fully opened: Apex: Close to 2A. Mid-section: Close to 145C to 145D. Base: Close to 150D.

*Involucral bracts.*—Length: About 5 mm to 8 mm. Width: About 2 mm to 4 mm. Shape: Ovate. Apex: Rounded. Base: Rounded to truncate. Margin: Entire.

Texture, upper and lower surfaces: Smooth, glabrous. Number per inflorescence: About 25 to 30 arranged in about two or three whorls. Color, upper surface: Close to 137C. Color, lower surface: Close to 137A.

*Peduncles.*—Length, terminal peduncle: About 4.5 cm. Length, fourth peduncle: About 6.5 cm. Diameter: About 2 mm. Strength: Moderately strong. Angle: About 30° from the flowering stem axis. Texture: Pubescent. Color: Close to 146A.

*Reproductive organs.*—Androecium: Not observed. Gynoecium: Present on both ray and disc florets. Style length: About 4 mm. Style color: Greenish. Stigma color: Yellow.

*Seed/fruit.*—Seed and fruit production have not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekstarga' as illustrated and described.

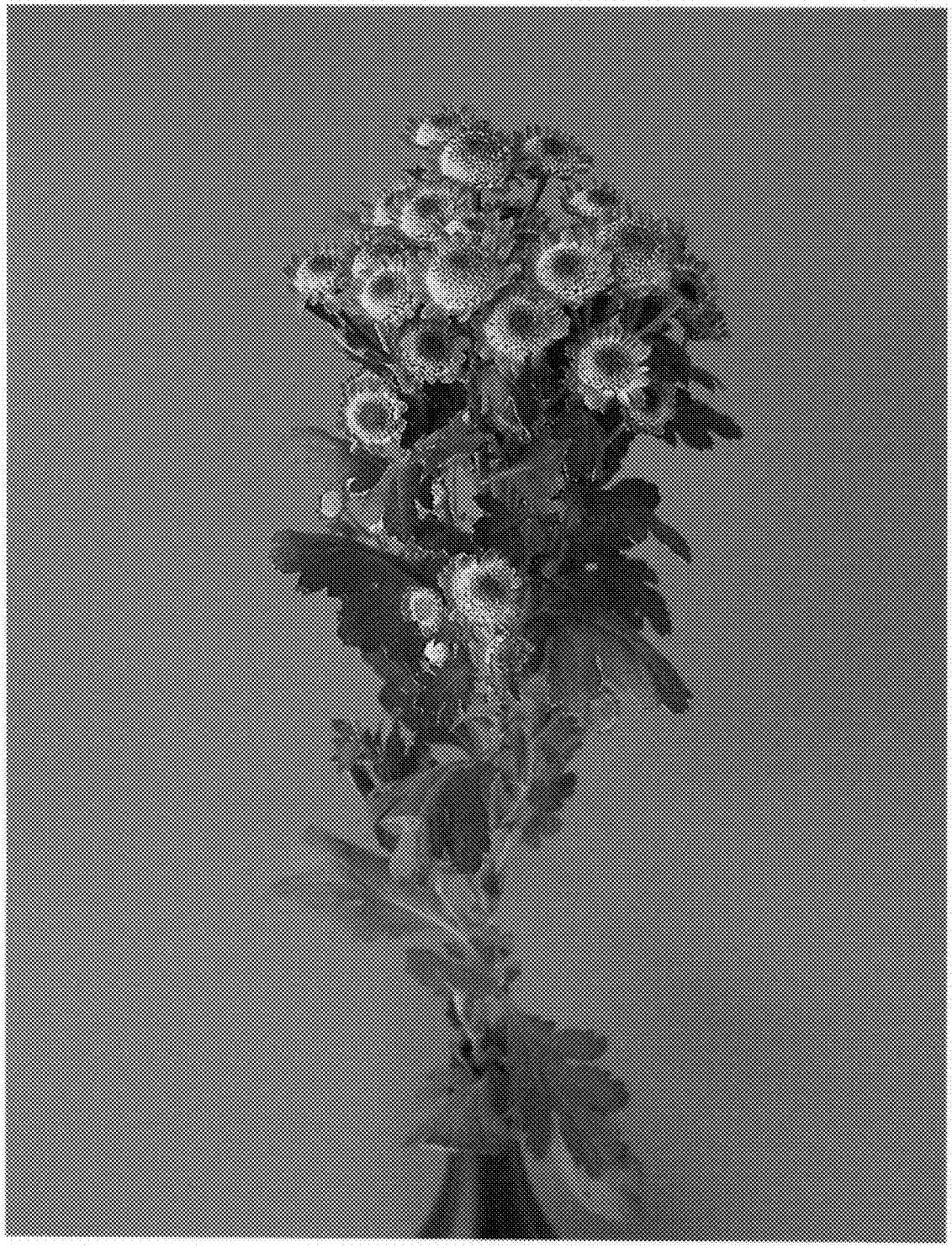

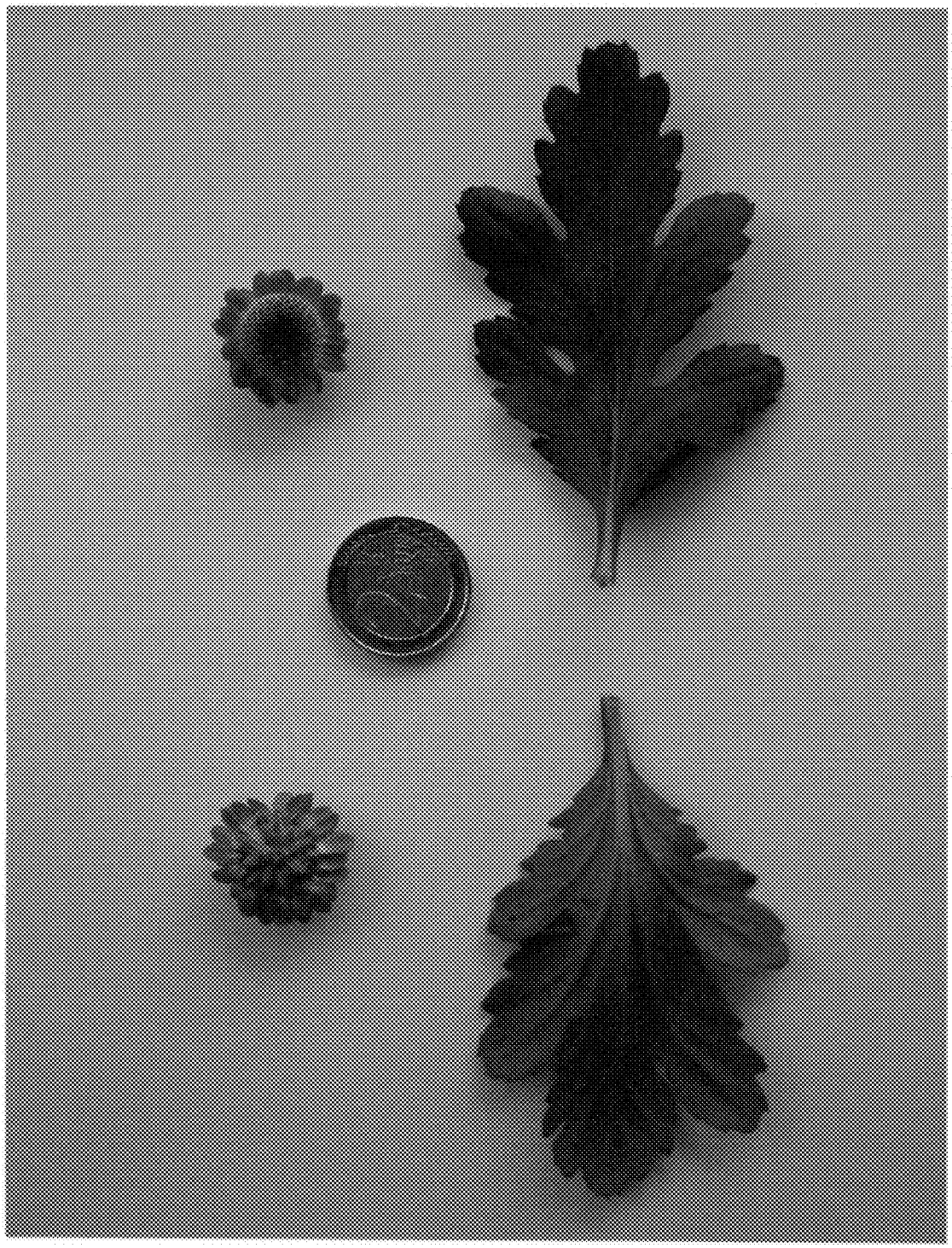

* * * * *